United States Patent [19]
Clark

[11] Patent Number: 6,142,927
[45] Date of Patent: Nov. 7, 2000

[54] METHOD AND APPARATUS FOR TREATMENT WITH RESONANT SIGNALS

[76] Inventor: James Hoyt Clark, 432 N. 750 E., Lindon, Utah 84042

[21] Appl. No.: 09/152,195

[22] Filed: Sep. 14, 1998

[51] Int. Cl.$^7$ ..................................................... A61N 2/00
[52] U.S. Cl. .............................................. 600/9; 128/897
[58] Field of Search .................................... 600/9–15, 26; 128/897–98, 905

[56] References Cited

U.S. PATENT DOCUMENTS

| | | | |
|---|---|---|---|
| 3,773,049 | 11/1973 | Rabichev et al. | 128/362 |
| 4,779,593 | 10/1988 | Kiernan | 128/422 |
| 4,821,725 | 4/1989 | Azam | 128/420 |
| 5,413,587 | 5/1995 | Hochstein | 607/100 |
| 5,437,658 | 8/1995 | Muller et al. | 606/5 |
| 5,507,791 | 4/1996 | Sit'ko | 607/101 |
| 5,626,617 | 5/1997 | Brewitt | 607/2 |
| 5,690,109 | 11/1997 | Govind et al. | 128/653.2 |

OTHER PUBLICATIONS

Chen K, Applying quantum interference to EDST medicine testing, IEEE Engineering in Medicine and Biology, 5:3, 64–66, May/Jun. 1996.

Krop J. Swierczek J, Wood A, Comparison of ecological testing with the Vega test method in identifying sensitivities to chemicals, foods and inhalants, Am J Acupunc, 1985; 13(3):253–9.

Popp F, Warnke U, Ksnig H, Peschka W, (Eds): Electromagnetic Bio-Information, Urban & Schwarzenburg, Munich, 1979.

Popp F, Nagl, W: A physical (electromagnetic) model of differentiation (parts 1 and 2), Cytobios, 37:45–83, 1983.

Reichmanis M, Marino AA, Becker RO, Electrical Correlates of Acupuncture Points, IEEE Transactions on Biomedical Engineering, 1975, 22:533–5.

Tiller WA, On the explanation of electrodermal diagnostic and treatment instruments, Part I: The electrical behavior of human skin, J Holistic Medicine, 4:105–127, 1982.

Voll R, The phenomenon of medicine testing in electroacupuncture according to Voll, AM J Acupunc, 8:9–104, 1980.

*Primary Examiner*—John P. Lacyk
*Attorney, Agent, or Firm*—J. David Nelson

[57] ABSTRACT

This invention is a method and apparatus for applying low energy, non-ionizing, nonthermal, electromagnetic radiation or electric current to the body of a subject for therapeutic and health promoting purposes. Digital sequences, referred to as product capsules, representing natural or manufactured substances are stored in a computer. The computer is interfaced with the apparatus of the present invention which generates electromagnetic signals or electric currents, referred to as product signals, corresponding to the product capsules, which have been found to stimulate a response in the human body of a subject which is equal or approximately equal to the response stimulated by the corresponding substances. The product signals resonate with the body of the subject at the cellular level. The apparatus provides for the application of the resonant product signals to the subject through an antenna, an infrared transmitter, audio speakers or direct contact to the skin.

90 Claims, 2 Drawing Sheets

Legend

1. Vertical axis-voltage
2. Horizontal axis-time/distance
3. Product signal
4. Wave amplitude
5. Wave separation
6. Wavelength
7. Square wave
8. DC product signal
9. Maximum DC current
10. DC Current wave form
11. Zero amplitude wave
12. Non-zero amplitude wave
13. Signal points
14. Minimum signal voltage

Legend

1. Vertical axis-voltage
2. Horizontal axis-time/distance
3. Product signal
4. Wave amplitude
5. Wave separation
6. Wavelength
7. Square wave
8. DC product signal
9. Maximum DC current
10. DC Current wave form
11. Zero amplitude wave
12. Non-zero amplitude wave
13. Signal points
14. Minimum signal voltage 15 Personal computer (PC)
16 Digital conductance meter receiver (DCMR)
17 Area of application
18 Body of subject
19 Digital conductance meter (DCM)
20 Personal capsule unit (PCU)
21 Personal TENS unit (PTU)
22 Capsule generator Unit (CGU)
23 Capsule imprinter unit (CIU)
24 Sample
25 Product signal
26 Product capsule and dilution capsule
27 Infrared transmitter (IFR)
28 Product capsules
   and dilution capsules
29 Frequency & amplitude adjusted capsules
30 Digital conductance meter footpedal (DCMF)
31 Product signal
32 Voice message
33 Audio recorder (REC)
34 AFFIRM (AFF)
35 Voice recording
36 Audio product signal
37 Headphone speakers
38 Headphone speakers
39 Software control
40 Input from DCM
41 Test probes
42 RF transmitter
43 Fiber optics applicator
44 DC signal
45 AC signal
46 Fiberoptics output
47 Infrared output
48 Wire
49 Electropads
50 Well
51 Substance
52 Wall transformer
53 Wire to RF transmitter
54 Wire to DC electropad
55 Wire to AC electropad
56 Wire to Fiberoptics
57 Wire to infrared transmitter
58 RF product signal

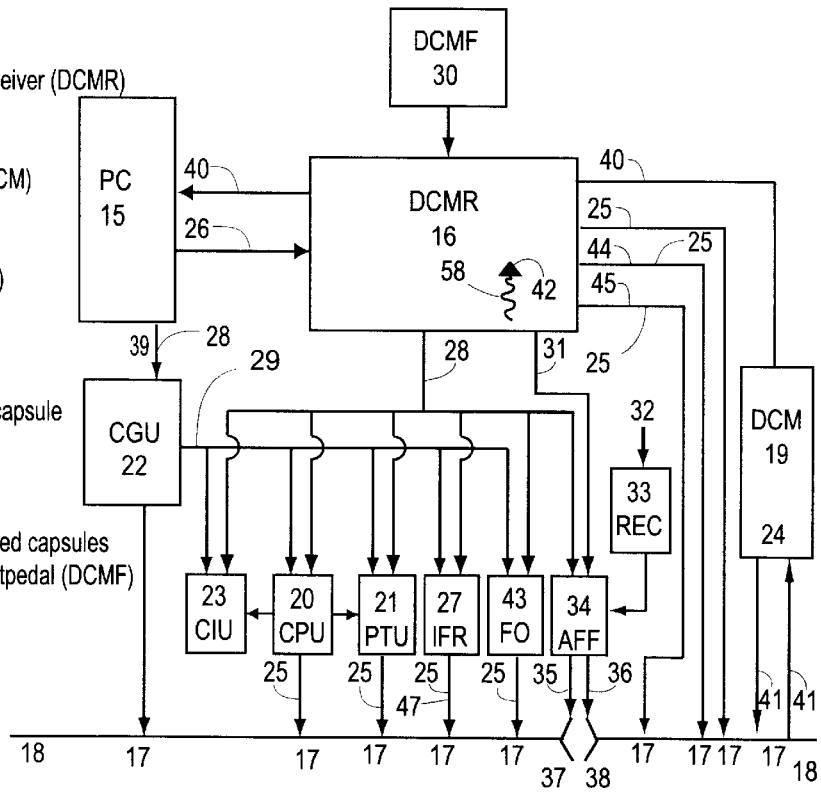

Fig. 3

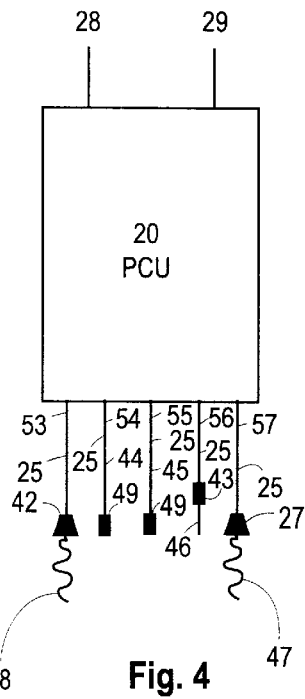

Fig. 4

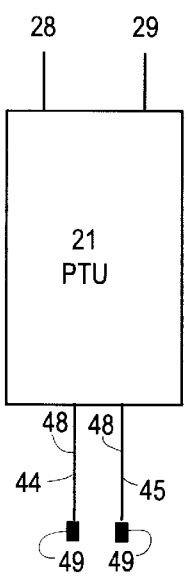

Fig. 5

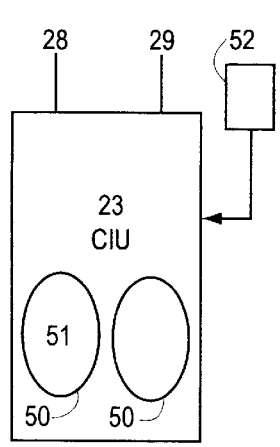

Fig. 6

METHOD AND APPARATUS FOR TREATMENT WITH RESONANT SIGNALS

FIELD OF THE INVENTION

This invention relates to methods and apparatuses for providing treatment or promoting health through the application of electromagnetic radiation or electric current to the body and in particular to methods and apparatuses for providing therapeutic treatment and promoting health of the body or for treating food, chemical, vitamin, mineral, metal, and biological sensitivities, through the application of electromagnetic radiation to the body in the form of signals of nonionizing, nonthermal, low energy, frequency specific electromagnetic radiation or low voltage alternating or direct current.

BACKGROUND OF THE INVENTION

The development of an ohmmeter to define the electronic characteristics of acupuncture points began with the discoveries by Yoshio Nakatani in Japan (Nakatani, 1956) and J. E. H. Niboyet (Niboyet, 1958), Bratu (Bratu, 1960), Brunet (Brunet, 1959, 1960), Voll (Voll 1976–7, 1980, 1978, 1983) and Wing (Wing, 1977) in Europe. They discovered that the acupuncture points were characterized by a lower resistance than the surrounding skin.

The measurement of the electrical properties of acupuncture points is based on scientific concepts and formulas (Reichmanis 1975, 1977, Tiller 1982, Chen 1996). The electrical properties of the skin and of the acupuncture points have been studied for years (Rosendal 1943, Nakatani 1956, Niboyet 1958, Lawler 1960, Zhu 1981, Tsuei 1996). Studies have shown that each acupuncture point has a lower resistance (higher conductance) than the surrounding skin. Commercial equipment has been developed to exploit the resistance properties of the acupuncture points (Saita 1973, Borsarello 1971, Tiller 1972, Matsumoto 1973, Voll 1978, Schimmel 1980).

The commercial equipment used the results of research (Rosendal 1943, Nakatani 1956, Niboyet 1958, Tiller 1972, Tsuei 1996) to define the parameters of the resistance values. The research found that a healthy or balanced subject has an optimal resistance value of 100,000 ohms. Lower resistance values correlate with inflammation processes in the body and higher resistance values correlated with degenerative processes in the body (Tsuei 1996).

Commercial equipment thus allows the operator to measure the resistance value at selected acupuncture points. It has been noted that if an operator places a substance near the subject, with all other variables unchanged, and repeats the measurement and the resistance value is balanced, then the substance is considered a source of balancing. If the resistance value was more unbalanced, then the substance is considered a source of provoking.

The substance could be anything found in nature or manufactured, including food, chemical, animal dander, pollen, pharmaceutical drug, homeopathic remedy, herbal, vitamin, mineral or biological organism. Fritz-Albert Popp, a German physicist, has investigated the resonance frequencies of substances and their actions in biological self-regulation. The nervous and chemical systems of the body are recognized as important mechanisms for the self-regulation of the body. Popp and his associates have presented the concept of another bio-information mechanism where the changes in the coherent electromagnetic fields of localized tissue produce bio-photon emissions (Popp, 1979, Popp, 1983). Kuo-Gen Chen, a Professor of Physics at Soochow University in Taiwan, considers that the primary mechanism is the changes in the quantum states of the tissue (Chen, 1996). The interactions to stimuli are at the molecular level (Popp 1979, Popp, 1983, Becker 1990).

A stimulus is anything that can produce a biological response or effect, a bioeffect, and can include any physiological or anatomical change from enzyme production to music to x-rays to emotions. All the bioeffects from electrical and magnetic energy are studied in the field of Bioelectromagnetics (BEM). An article from the National Institute of Health (NIH) summarizes the past research on BEM (Rubik, 1996). The report establishes that low energy signals produce a bioeffect (Tenforde 1987). The NIH articles states that in basic BEM research "Nonionizing, nonthermal exogenous EM fields exert measurable bioeffects in living organisms. In general, the organism's response to applied EM fields is highly frequency specific and the dose-response curve is nonlinear (i.e., application of an additional amount of the EM field does not elicit a response of equal magnitude; the response eventually diminishes no matter how additional EM stimuli are applied). Extremely weak EM fields may, at the proper frequency and site of application, produce large effects that are either clinically beneficial or harmful."

A number of devices have been developed for the application of electromagnetic radiation for treatment or health benefit purposes. In U.S. Pat. No. 3,773,049 to Rabichev et al., there are apparatuses disclosed which provides for the administration of very high frequency (VHF) frequency electromagnetic radiation simultaneously with light, sound and heat to treat neuropsychic and somatic disorders of inorganic origin. This invention works by posting a rhythmic and remotely controlled action of at least three of the stimuli upon the subject's nervous system. This device works primarily through a visual and auditory stimuli to the nervous system, with the VHF frequency electromagnetic radiation being applied simultaneously to the body.

In U.S. Pat. No. 4,779,593 to Keiernan an apparatus is disclosed for applying pulses of VHF radiation to the body for therapeutic purposes. This device includes a pulse control display circuit arrangement for selecting and controlling the pulse repetition frequency, amplitude and duration which is dependent upon the various values selected from the control panel. Radiation is applied to the body by a treatment head which is connected to pulse generator system by an articulated arm.

U.S. Pat. No. 4,821,725 to Azam et al discloses an apparatus for the treatment of the body through the inducement of hyperthermia by the application of an electromagnetic field to a target body area through two electrodes posed adjacent to or in the diseased or target area of the body. The two electrodes are connected to a transmitter which generates the signal for application to the body.

U.S. Pat. No. 5,413,587 to Hochstein discloses an apparatus for inducing hyperthermia in a target area of the human body for treatment of disease or the therapeutic benefits attributable to hyperthermia, through the application of black body infrared radiation. This device included a mechanism for limiting the transmission of heat by convection from the radiation source.

U.S. Pat. No. 5,437,658 to Muller et al. discloses a device for applying electromagnetic radiation to the cornea of the eye of a subject for the purpose of modifying the curvature of the cornea. The device provides for application of electromagnetic radiation of a selected wave length to which is suitable for absorption by the stroma the cornea and incorporates multiple irradiation ports, each with a fiberoptic feed, for the application of the radiation as needed to accomplish the desired reshaping of the cornea, thereby correcting the vision of the subject U.S. Pat. No. 5,507,791 to Sit'ko discloses a method of treating the subject by applying electromagnetic radiation in the microwave frequency range to a set of biologically active points. The frequency and power of the radiation applied is varied so as to determine a frequency and power level which promote a steady response reaction of the subject in the desired area of treatment.

U.S. Pat. No. 5,626,617 to Brewitt discloses a method for medical disorders through the administration of electromagnetic signals in the radio frequency range, these radio frequency signals being selected to produce the same physiological response as certain homeopathic solutions.

While each of the devices disclosed in the prior art appears to have provided a means for achieving the apparent objectives for the device, none of the inventions disclosed in the prior art achieves several of the objectives of the present invention. Furthermore, the present invention provides improved capabilities for achieving a number of the objectives of the inventions disclosed in the prior art.

It is an objective of the present invention to provide a method and apparatus for producing sequences of binary numbers called "product capsules" which can be used to generate electromagnetic signals called "product signals" which stimulate a response from the body of a subject which equals or approximates the response stimulated by a variety of natural and man made products and other stimuli, all of which are herein referred to collectively as "products".

It is a further objective of the present invention to provide a method and apparatus for generating and applying product signals to the body of a subject.

It is a further objective of the present invention to provide a method and apparatus for applying product signals to selected substances to imprint the response characteristics of the products on the substances.

It is a still further objective of the present invention to provide portable hand held units for storing product capsules, for generating product signals from the stored product capsules and for applying the signals to the body of a subject at times and locations desired by the subject or directed by a health care provider.

It is a still further objective of the present invention, to provide a method and apparatus for recording verbal messages and administering them simultaneously to a subject with audio signals which are generated based upon product signals.

SUMMARY OF THE INVENTION

This invention is based on the simulation of the resonant signal of a product through the use of a sequence of digital values. The sequence of digital values is used to generate highly frequency specific, nonionizing, nonthermal low energy signals in the form of electromagnetic radiation or electric current to cause a positive health effect on the body of a subject. The signals include all those frequencies from direct current to infrared that are nonionizing as shown in Table 1 below.

TABLE 1

Electromagnetic Spectrum

| Frequency rage (Hz)* | Classification | Biological effect |
|---|---|---|
| 0 | Direct Current | Nonionizing |
| $0-10^9$ | Alternating Current | Nonionizing |
| 0–300 | Extremely low frequency | Nonionizing |
| $300-10^4$ | Low frequency | Nonionizing |
| $10^4-10^9$ | Radio frequency | Nonionizing |
| $10^9-10^{12}$ | Microwave and radar bands | Nonionizing |
| $10^{12}-4 \times 10^{14}$ | Infrared band | Nonionizing |
| $4 \times 10^{14}-7 \times 10^{14}$ | Visible light | Weakly ionizing |
| $7 \times 10^{14}-10^{18}$ | Ultraviolet band | Weakly ionizing |
| $10^{18}-10^{20}$ | X rays | Strongly ionizing |
| Over $10^{20}$ | Gamma rays | Strongly ionizing |

*Division of the EM spectrum into frequency bands is based on conventional but arbitrary usage in various disciplines. From Rubik, 1996.

The purpose of the signal is to resonate with the body at the cellular level. Studies have established that the body is changed by small amounts of electrical and magnetic energy that form a resonant signal with the body (Popp 1979, Rubik 1994).

The source of the resonant signal is a series of digital zeros and ones and is called a product capsule. A product signal is generated based upon the product capsule. A "zero" value in the sequence of numbers comprising the product capsule, results in a zero amplitude wave at the corresponding point in the product signal. A "one" results in a non-zero voltage amplitude wave of a selected value, such as 5 volts, at the corresponding point in the product signal. A product capsule can be made that simulates the resonance of any product, where the sequence of zeros and ones in the capsule is selected by measuring the electrical resistance of an acupuncture point using a sample of the product and then finding a product capsule, by trial and error, that causes the same response in the subject.

The process is like listening to a piano and making a digital circuit produce the same sound. The process is begun by measuring the base resistance reading at an acupuncture point or other test point or series of test points on the body of the person. Then a sample of a product is introduced to the person that changes the resistance readings. After the sample is removed, a product capsule is made of a specific sequence of binary zeros and ones so the sequence results in the generation of a product signal which causes the same changes in the resistance readings at the test points as the product. For certain preferred embodiments, the capsule will be ten bytes or eighty bits in length. For other preferred embodiments the capsule will be whatever length is required for the binary sequence which simulates the product. The sequence is set with a computer program that enables the change of each bit in a capsule.

The dose or dilution is also managed as a capsule. The NIH stated that "the dose-response curve is nonlinear." In pharmaceuticals and homeopathics, the amount of the substance is important (Benveniste 1993). In pharmaceuticals, the amount is based on the mass of the body. In homeopathics, the amount is based on the resonant imbalance of the body. In homeopathics, the more diluted the substance, the more energetic the substance. A capsule is created for each desired dilution value.

A Digital Conductance Meter Receiver, a DCMR, is attached to the serial port of a computer which contains the software to operate the apparatus of the present invention. The DCMR enables the computer to interface with an ohmmeter and the other components. The DCMR communicates with the ohmmeter by RF signal. The DCMR generates product signals based upon the product capsules selected from the product capsule library stored in the attached computer. The product signals are applied to the body of the subject by the DCMR through RF transmission from an internal antenna located in the DCMR, by an infrared transmitter connected to the DCMR, or by a wire which transmits a current to one or more pads on the desired area of application on the body of the subject. Alternatively, selected product capsules and dilution capsules are down loaded to a portable, hand held Personal Capsule Unit, a PCU, or to a portable, hand held Personal Tens Unit, a PTU, where they are used for remote generation and application of product signals to the subject, by RF transmission, infrared transmission, other electromagnetic signals, audio signals including musical signals, or electric current. Other optional components include a capsule imprinter unit for exposing substances to product signals and an affirm unit for producing an audio signal which comprises a message recorded by the subject played for one ear and a product signal for the other ear. An optional capsule generator unit can also provide greater flexibility and control in the frequency and intensity of product signals and in the construction of series of product signals.

For certain preferred embodiments, the bits of the product capsule and the dilution capsule produce a changing voltage that produces a square wave with a modulated frequency. The body has components that are equivalent to an RC circuit (Tiller 1972, Chen 1996). The invention uses the RC characteristic of the body. Since the RC component has slow response, the signal resonates. The body receives the resonating signal of the capsules at the cellular level. The NIH article (Rubik 1996) presents research that proposes the cell membrane as the primary site of transduction of EM field bioeffects and states "Relevant mechanisms may include changes in cell-membrane binding and transport processes, displacement or deformation of polarized molecules, modifications in the conformation of biological water (i.e., water that comprises organisms), and others." Dumitrescu (Dumitrescu 1971) has stated that the change can be in the anatomy and physiology of the organs and tissues of the body.

Capsules have been made by the present inventor for about 40,000 products. The capsules have been shown to produce a balance that may last for only a few seconds, may last for a longer period of time, or may be permanent.

The various methods of application, which include an antenna, an infrared transmitter, a speaker, fiber optic cable or direct electrical contact allows the capsules to be applied at varying distances from the body and for varying durations.

BRIEF DESCRIPTION OF DRAWINGS

FIG. 3 is a schematic block diagram of a preferred embodiment of the apparatus of the present invention.

FIG. 4 is a schematic block diagram of a preferred embodiment of a personal capsule unit of the present invention.

FIG. 5 is a schematic block diagram of a preferred embodiment of a personal tens unit of the present invention.

FIG. 6 is a schematic block diagram of a preferred embodiment of a capsule imprinter unit of the present invention.

DETAILED DESCRIPTION OF PREFERRED EMBODIMENTS

The present invention provides for the application of a resonant electromagnetic signal or current to the human body or to a specific area of the body. The resonant signals are designed to cause a response effect in the body of the subject which is identical to or approximates the effect of a stimulus, which is referred to herein as a "product". For preferred embodiments, the simulated product will be a natural or manufactured substance such as a food, a chemical, animal dander, pollen, pharmaceutical drug, homeopathic remedy, herb, vitamin, mineral, or a biological organism. These signals are applied for a therapeutic treatment or for promoting health of the body. Examples of therapeutic treatment and health promoting purposes includes treatment of food, chemical, vitamin, a mineral, metal and biological sensitivities. Preferred embodiments utilize electromagnetic radiation signals or electric currents at frequencies and intensities which are non ionizing, non thermal and are frequency specific.

Figure 1:
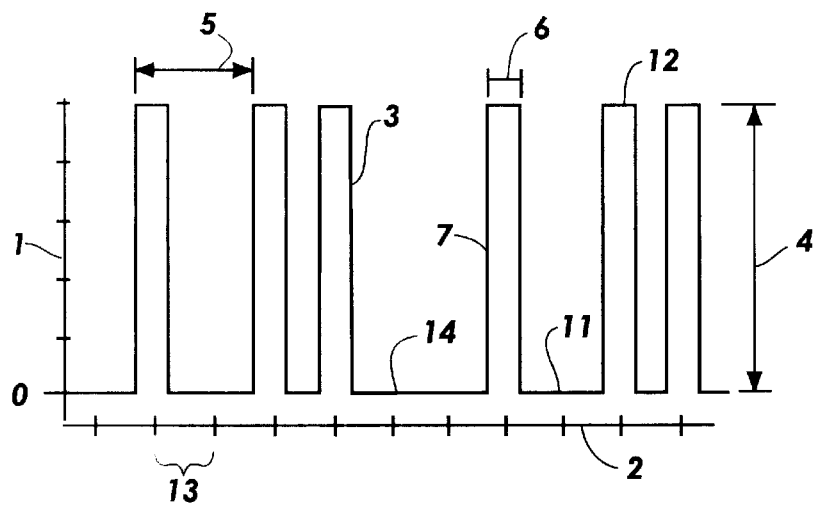
FIG. 1 is an illustration of a preferred embodiment of a product signal in the form of a square wave for the present invention.

An example of a product signal is shown in FIG. 1. For this example, the product signal 3 consists of a series of square waves 7 of uniform amplitude 4 and a wavelength 6. Voltage is represented on the vertical axis 1 and time/distance is represented by the horizontal axis 2.

Other embodiments may utilize electromagnetic signals with different wave forms such as sinusoidal waves or triangular waves. In addition to varying the amplitude between zero volts and a pre-selected fixed positive voltage to correspond to the product capsule, the wavelength or frequency may also be varied as desired to provide a product signal which enhances the match of the response to the response of the simulated product.

Figure 2:
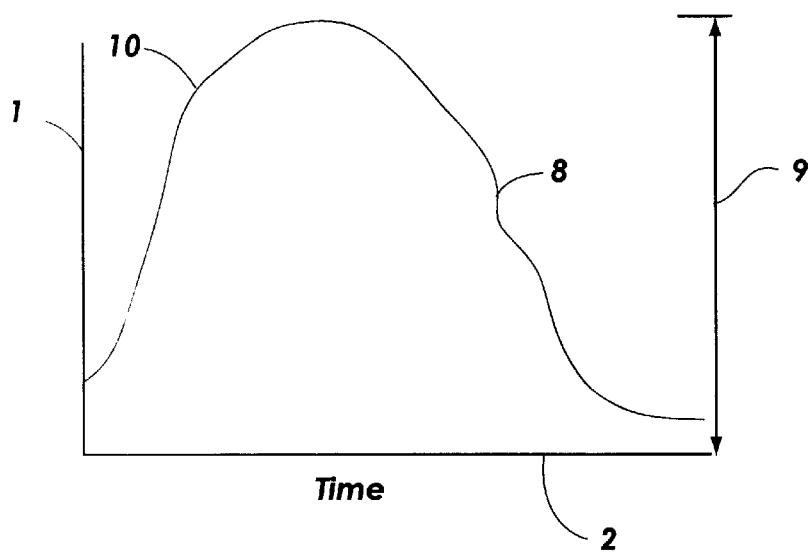
FIG. 2 is an illustration of a preferred embodiment of a product signal in the form of a direct current for the present invention.

Other embodiments may also provide for the administration of electric current to a point of application, to illicit the desired response. These embodiments may utilize alternating current or direct current. FIG. 2 illustrates a typical direct current product signal 8. For these embodiments the maximum current 9 and the form of the current curve 10 can be varied to equate or approximate the product response for the product being simulated.

Referring again to FIG. 1, for most preferred embodiments of the present invention a product signal is derived from a sequence of digital zeroes and ones, known as a product capsule. The digital values are manifested in the product signal as the amplitudes of a series of waves 7 which have a zero amplitude 11 or a pre-selected non-zero amplitude 12 depending upon whether the corresponding value in the product capsule sequence at the signal point 13 is zero or one. Alternatively, for other embodiments, the minimum signal voltage 14 can be a positive value or a negative value. Also, as indicated above, other wave forms can be used in half cycle or full cycle wave forms. For example, a product signal can be comprised of a series of half cycle or full cycle sinusoidal waves with either a zero amplitude or a pre-selected amplitude at each specific signal point depending upon whether the corresponding product capsule value is a zero or one at that signal point.

For preferred embodiments product signals are generated as highly frequency specific, non ionizing, non thermal low energy signals in the form of electromagnetic radiation or electric current. For preferred embodiments, the signals include all electromagnetic radiation frequencies from very low frequency radiation to infrared that are nonionizing. Weakly ionizing frequencies may also be used for certain embodiments for specific treatment purposes. While strongly ionizing frequencies might be used to achieve certain specific purposes, the negative effects of such radiation is considered by the inventor to offset any possible benefit. DC current or AC current of a wide range of frequencies is also used for certain preferred embodiments. The product signal is selected to resonate with the body at the cellular level.

A product signal can be generated which simulates the resonance effect of any product. The sequence of zeroes and ones in the product capsule for a particular product is selected by comparing the response of the body at selected points, typically acupoints, to the product signal being tested and the response at the same points of the product being simulated.

For certain preferred embodiments, the process of determining a product capsule which can be used to generate a product signal which causes a body response which equals or approximates the response of the body to a specific substance or product begins with the measurement of the electrical resistance at selected test points, which are commonly acupoints. When a sample of the product to be simulated is introduced into the presence of a subject, changes in the resistance reading at one or more of the test points on the body of the subject will normally occur. After the sample of the product to be simulated is removed, trial product capsules are constructed from binary zeroes and ones from which product signals are generated and tested on a trial and error basis until a product capsule is found from which a product signal is generated which produces the same change in resistance at the test points as the substance which is to be simulated. For certain preferred embodiments, the product capsule will be ten bytes or eighty bytes in length. However, any length of signal can be used which results in a closer response match by a product signal as compared to the product. The sequence of zeroes and ones which comprises the product capsule is then input to a computer program that enables the generation on demand of a product signal in the form of an electromagnetic signal or electric current corresponding to the digital values of the product capsule.

The dose or dilution of the product signal is also managed as a dilution capsule. A dilution capsule is created for each desired dilution value. For certain preferred embodiments, the dilution capsule is made up of the logarithm of the desired dilution value times the power of dilution. For example, for a homeopathic remedy with a desired dilution of 5x, the value is 5 and the power, x, is 10 which gives a result of 50. The log of 50 is 1.699.

Referring to FIG. 3, while certain embodiments incorporate computational capabilities which allow the apparatus of the present invention to stand alone, because of cost considerations most preferred embodiments rely on an interconnection 26 & 40 with a personal computer, a PC 15, or a network. When a Personal Capsule Unit, a PCU 20 or a Personal Tens Unit, a PTU 21, is used, an interface with a computer 15 is needed only periodically to allow updates or changes in the product capsules and dilution capsules stored in the PCU or PTU. When neither a PCU or a PTU is utilized, an active interface with a computer is required for these preferred embodiments.

Certain preferred embodiments use a product capsule and a dilution capsule together to produce a series of wave forms of changing voltage that is embodied in a product signal. Under certain preferred embodiments, the product signal is a series of square waves as illustrated in FIG. 1. The human body has electrical characteristics that result in a response to a electromagnetic signal, whether as electromagnetic radiation or as electric current, which is similar to that of a RC circuit. The present invention uses the RC characteristic of the body. Since the RC component slows the response to the product signal, the signal resonates. The body receives the resonating signal of the product capsules at the cellular level which leads to the therapeutic or health benefit effect.

Preferred embodiments of the method of the present invention include the following steps. A product capsule is selected based on a particular therapy or benefit desired and a dilution capsule is selected to provide the desired strength of the product signal to be applied. The product capsule and the dilution capsule are used together to produce a product signal with the desired sequence of waves and the desired amplitude. This product signal is then applied to the body with the intent to produce a specific desired response.

The initial step in certain preferred embodiments of the method of the present invention is to determine the electrical resistance of one or more selected acupoints or other specific application points, if the product signal is to be applied to a specific area of the body of the subject 18, or to determine the electrical resistance of a number of test points, if the product signal is to be applied generally to the entire body of the subject. Referring again to FIG. 3, this is accomplished for most embodiments through use of a specially designed hand held ohmmeter, referred to herein as a Digital Conductance Meter, a DCM 19, which measures the resistance at a test point 17 through a test probe 41 placed against the skin at the test point. A ground probe is generally grasped in the hand of the subject on the side of the subject's body opposite the test point. The resistance measurement 40 is then transmitted to a Digital Conductance Meter Receiver, a DCMR 16. For certain preferred embodiments, a Digital Conductance Meter Footpedal, a DCMF 30, is used by the operator to activate and deactivate the resistance measurement transmission to the DCMR as a resistance measurement is taken. The DCMF increases the ease of operation of the DCM by the operator and also makes it possible for the subject to make a resistance measurement on his own body and simultaneously transmit the measurement to the DCMR at a desired moment. The DCM transmits the resistance readings to the DCMR by air, wire or fiberoptic cable. For ease of operation, RF communication between the DCMF and the DCM, and between the DCM and the DCMR is utilized by most preferred embodiments. For the embodiment shown in FIG. 3, the DCMR receives the resistance readings and sends the data to the PC. Operating software in the PC provides storage of the resistance readings for comparison with the values after application of the product signal.

As shown in FIG. 3, the DCMR may also be periodically connected to an optional Personal Capsule Unit, a PCU 20, or an optional Personal Tens Unit, a PTU21. The PCU's and the PTU's are hand held, portable units used for the storage and subsequent remote administration of product signals to the body of a subject.

The operating software contains the library of products and their corresponding product capsules. The dilution capsules are also contained in the operating software.

The health care practitioner or other operator can select one or more product capsules and dilution capsules and the selected product capsules and dilution capsules are transmitted from the PC to the DCMR. The DCMR combines the product capsules and the dilution capsules in a manner determined by the operator and generates one or more product signals 28. The product signals may be generated as radio frequency signals 58 transmitted from a RF transmitter 42 in the DCMR. Certain preferred embodiments of the DCMR RF transmitter incorporate a special antenna specifically designed for optimum RF transmission of the product signals. Product signals may also be generated as infrared signals 47 from a separate infrared transmitter 27 connected by wire, fiber optic cable or RF communication with the DCMR. Similarly, a fiber optic applicator 43 may be used to administer a product signal in certain frequencies directly to a desired area of application on the body of the subject. Also, product signals may be applied directly to the body of the subject as a low voltage direct current 44 or a low voltage alternating current 45.

For the embodiment shown in FIG. 3, product signals generated and transmitted by the DCMR are generated by the DCMR by utilizing product capsules and dilution capsules transmitted from the PC. Alternatively, for other preferred embodiments, one or more product capsules and one or more dilution capsules can be received by the DCMR from the PC and transmitted by the DCMR to a PCU where they are stored for later generation, transmission and administration of product signals to the body of a the subject. Referring to FIG. 4, product signals 25 may be generated, transmitted and applied by the PCU as RF 58, infrared 47, or other frequency waves or as direct current 44 or alternating current 45 in manners similar to that provided by direct application from the DCMR. Application of the PCU generated product signals can be by RF transmitter 42, wire 54 & 55, separate connected infrared transmitter 27, or direct fiber optic cable 46 transmission. The storage of one or more product capsules and one or more dilution capsules in the PCU allows for remote and repetitive application of one or more desired product signals without an intervening interface with the DCMR and the PC. While the application of the desired product signal by a health practitioner can be readily accomplished by the embodiments shown in FIG. 3, for the subsequent repetitive application of product signals by the subject at times and locations desired by the subject or his health care practitioner, the small, portable PCU illustrated in FIG. 4 is needed.

The PCU can also be used in conjunction with a Personal Tens Unit, a PTU 21, which is shown in FIG. 5, or the PTU can be connected directly to the DCMR as shown in FIG. 3. The PTU can be loaded with one or more product capsules and one or more dilution capsules either directly from the DCMR or from a PCU. The PTU is then used for the remote and repetitive generation, transmission and application of product signals in the form of direct current 44 or alternating current 45 at times and locations desired by the subject or his health care practitioner. The direct current or alternating current is typically transmitted by the PTU by wire 48 to electro pads 49 for tactile stimulation as shown in FIG. 5. The electric current generated by the PTU may follow a square wave pattern in a form similar to that shown in FIG. 1, or can be a half cycle or full cycle wave in a sinusoidal, triangular wave or other wave form or can follow a wave form similar to that shown in FIG. 2.

Either or both the PCU and the PTU can be worn by the subject and can be programmed to administer one or more product signals at desired times with a desired number of repetitions. As with the DCMR, for preferred embodiments of the PCU, the frequency and the intensity of the product signal can be adjusted. Similarly, for preferred embodiments of the PTU, the frequency of the signal can be increased or decreased and the intensity of the product signal, and thus the applied current, can be increased or decreased as desired by the practitioner or the subject.

Certain preferred embodiments also include a capsule imprinter unit, a CIU 23, as shown on FIG. 3. A capsule imprinter unit is used to apply one or more product signals to a selected substance. Referring to FIG. 6, the CIU has a well 50 where the selected substance 51 can be placed. The CIU is then connected to a DCMR or a PCU as shown in FIG. 3. Selected product capsules and dilution capsules 28 or selected product signals are transmitted by the DCMR or PCU to the CIU. The product signal is then applied to the substance in the well by antenna emission of the product signal or by passing the product signal through a coil surrounding the substance. A product signal can be reapplied to the substance as many times as desired or a series of product signals can be applied to the substance. The CUI may also contain two or more wells 50 as shown in FIG. 6, thereby providing for simultaneous or alternating application of the same or different product signals or series of product signals to one or more substances.

Certain preferred embodiments of the CIU incorporate a wall transformer 52 as shown in FIG. 6. For certain preferred embodiments, a plurality of wells of varying sizes may be incorporated to accommodate varying quantities of the selected substances from as small as a fraction of a gram up to several grams or more. Certain embodiments of the CIU incorporate an output jack to which a conductor or fiberoptic cable is connected for transmitting product signals to an optional soft or hard coil that can accommodate a larger quantity of the substance to be imprinted. Some preferred embodiments also incorporate one or more high intensity Xenon or other types of strobe lights to excite the substance to be imprinted and to show operation. The flash duration, intensity and frequency can be fixed or adjustable.

Referring again to FIG. 3, a Capsule Generator Unit, a CGU 22 may be utilized with embodiments which operate with one or more product capsules and one or more dilution capsules transmitted from the DCMR or from a PCU. For preferred embodiments the CGU is a signal generator using digital circuitry to produce a product signal in a desired wave form based on product capsules and dilution capsules received from the DCMR or PCU. For certain preferred embodiments the CGU will generate product signals with a frequency in the range of 0.001 Hz to 3.5 MHZ. The frequency of the product signals can be adjusted by the practitioner or the subject by controls on the CGU. Also, certain preferred embodiments of the CGU, multiple frequencies can be selected within the range of the generator and controls can be used to switch between the multiple selected frequencies or to program a switch as desired by the practitioner or the subject. This can be used to attempt to maximize a response by fine tuning the frequency or can be used to apply a product signal at a selected frequency and at a harmonic frequency, alternatively. Preferred embodiments of the CGU also incorporate a selector switch for selection of a square wave, sine wave, bi-polar square wave, triangular wave, digital square wave or other wave forms. Output gain or signal strength for the product signals can also be digitally adjusted by the user. Typically the frequency selection and signal intensity are controlled by a digital keypad on the CGU.

Referring further to FIG. 3, preferred embodiments of the present invention may also incorporate an affirm unit 34. An affirm unit is preferably a small hand held device with a verbal message loaded on it by the user. The affirm unit generates a resonate signal from an audio message 32 which is recorded 33 by the user. Under certain preferred embodiments of the method of the present invention, the user selects an interval time and the affirm unit plays the verbal message repeatedly for the user at the interval selected. Under preferred embodiments, the message 35 is played at the normal frequency of the voice of the user on one speaker 37 and a different resonate frequency 36 in the other speaker 38.

The operating software program which is loaded in the PC allows the user to select the product and dilution capsules and to output one or more product capsules, one or more dilution capsules to the DCMR. The operating software program also displays and records initial and subsequent resistance readings as measured at test points or application points.

What is claimed is:

1. Apparatus for administering, to a desired area of application on a human body of a treatment subject, one or more therapeutic electromagnetic signals of electromagnetic waves or electric currents, each said signal stimulating a response in said human body which equals or approximates a response stimulated by a product corresponding to said signal, said apparatus comprising:
   a) generating means for generating said electromagnetic signals, each said signal being a function of a sequence of binary numbers representing a corresponding product;
   b) applying means for applying said electromagnetic signals to said area of application.

2. Apparatus as recited in claim 1 further comprising a producing means for producing and storing said sequences of binary numbers.

3. Apparatus as recited in claim 2 wherein said producing means comprises:
   a) a computer and operating software for generating and storing trial sequences of binary numbers and for receiving, storing and comparing electrical resistance measurements;
   b) an electrical resistance meter and probe for testing the electrical resistance of one or more test points on a human body of one or more test subjects before and after application of electromagnetic signals generated as a function said trial sequences of binary numbers;
   c) a resistance meter receiver for receiving said resistance measurements from said resistance meter and transmitting said resistance measurements to said computer.

4. Apparatus as recited in claim 2 wherein said producing means further comprises means for producing and storing a plurality of dilution factors and wherein said functions utilize said dilution factors with said sequences of binary numbers to vary the amplitude of said electromagnetic signals.

5. Apparatus as recited in claim 1 wherein said generating means comprises a computer and operating software providing for selecting one or more desired wave forms for said electromagnetic signals and generating said electromagnetic signals as a function of said sequences of binary numbers.

6. Apparatus as recited in claim 1 wherein said generating means comprises a computer and operating software providing for selecting one or more desired wave forms for said electromagnetic signals and generating said electromagnetic signals as a function of said sequences of binary numbers and as a function of one or more dilution factors.

7. Apparatus as recited in claim 1 further comprising a personal capsule unit for storing one or more said sequences of binary numbers and one or more dilution factors, generating one or more product signals as a function of said binary numbers and said dilution factors, and applying said product signals to said area of application.

8. Apparatus as recited in claim 1 further comprising a personal tens unit for storing one or more said sequences of binary numbers and one or more dilution factors, generating one or more electric current product signals as a function of said binary numbers and said dilution factors, and applying said product signals to said area of application.

9. Apparatus as recited in claim 1 wherein said applying means comprises a radio frequency transmitter and antenna.

10. Apparatus as recited in claim 1 wherein said applying means comprises an infrared transmitter.

11. Apparatus as recited in claim 1 wherein said applying means comprises a visible light transmitter and a fiber optic cable.

12. Apparatus as recited in claim 1 wherein said applying means comprises an electric current generator, one or more conductors and one or more electrical contact pads.

13. Apparatus as recited in claim 1 further comprising a capsule imprinter unit.

14. Apparatus as recited in claim 1 further comprising a capsule generator unit.

15. Apparatus as recited in claim 1 further comprising an affirm unit.

16. Apparatus as recited in claim 1 further comprising means for measuring the electrical resistance of said area of application.

17. Apparatus for administering one or more product signals to a desired area of application on a human body of a treatment subject comprising:
   a) generating means for generating one or more product signals, each product signal being a function of a product capsule;
   b) applying means for applying said product signals to said area of application.

18. Apparatus as recited in claim 17 further comprising producing means for producing and storing product capsules for one or more products.

19. Apparatus as recited in claim 18 wherein said producing means comprises:
   a) a computer and operating software for generating and storing trial product capsules and for receiving, storing and comparing electrical resistance measurements;
   b) an electrical resistance meter and probe for testing the electrical resistance of one or more test points on a human body of one or more test subjects before and after application of product signals generated as a function said trial product capsules;
   c) a resistance meter receiver for receiving said resistance measurements from said resistance meter and transmitting said resistance measurements to said computer.

20. Apparatus as recited in claim 18 wherein said producing means further comprises means for producing and storing a plurality of dilution capsules and wherein said functions utilize said dilution capsules with said product capsules to vary the amplitude of said product signals.

21. Apparatus as recited in claim 17 wherein said generating means comprises a computer and operating software providing for selecting one or more desired wave forms for said product signals and generating said product signals as a function of said product capsules.

22. Apparatus as recited in claim 17 wherein said generating means comprises a computer and operating software providing for selecting one or more desired wave forms for said product signals and generating said product signals as a function of said product capsules and as a function of one or more dilution capsules.

23. Apparatus as recited in claim 17 wherein said generating means comprises means for generating one or more product signals, each product signal being a function of a product capsule and a dilution capsule.

24. Apparatus as recited in claim 17 further comprising a personal capsule unit for storing one or more product capsules and one or more dilution capsules, generating one or more product signals as a function of said product capsules and said dilution capsules, and applying said product signals to said area of application.

25. Apparatus as recited in claim 17 further comprising a personal tens unit for storing one or more product capsules and one or more dilution capsules, generating one or more electric current product signals as a function of said product capsules and said dilution capsules, and applying said product signals to said area of application.

26. Apparatus as recited in claim 17 wherein said applying means comprises a radio frequency transmitter and antenna.

27. Apparatus as recited in claim 17 wherein said applying means comprises an infrared transmitter.

28. Apparatus as recited in claim 17 wherein said applying means comprises a visible light transmitter and a fiber optic cable.

29. Apparatus as recited in claim 17 wherein said applying means comprises an electric current generator, one or more conductors and one or more electrical contact pads.

30. Apparatus as recited in claim 17 further comprising a capsule imprinter unit.

31. Apparatus as recited in claim 17 further comprising a capsule generator unit.

32. Apparatus as recited in claim 17 further comprising an affirm unit.

33. Apparatus as recited in claim 17 further comprising means for measuring the electrical resistance of said area of application.

34. Apparatus as recited in claim 33 wherein said means for measuring the electrical resistance of said area of application comprises a DCM.

35. Apparatus as recited in claim 17 further comprising means for receiving and storing one or more product capsules and one or more dilution capsules.

36. Apparatus as recited in claim 35 wherein said means for receiving and storing one or more product capsules and one or more dilution capsules comprises a DCMR.

37. Apparatus as recited in claim 35 wherein said means for receiving and storing one or more product capsules and one or more dilution capsules comprises a PCU.

38. Apparatus as recited in claim 35 wherein said means for receiving and storing one or more product capsules and one or more dilution capsules comprises a PTU.

39. Apparatus as recited in claim 17 wherein said means for generating product signals as a function of product capsules comprises a CGU.

40. Apparatus as recited in claim 17 wherein said means for generating product signals as a function of product capsules and said means for applying said product signals to said area of application comprises a PCU.

41. Apparatus as recited in claim 17 wherein said means for generating product signals as a function of product capsules and said means for applying said product signals to said area of application comprises a PTU.

42. Apparatus as recited in claim 17 wherein said means for generating product signals as a function of product capsules and said means for applying said product signals to said area of application comprises a DCMR.

43. Apparatus as recited in claim 17 further comprising a CGU for storing one or more product capsules and one or more dilution capsules in memory, generating one or more product signals as a function of said product capsules and dilution capsules, and transmitting said product signals in one or more selected wave forms, one or more selected frequencies, and one or more selected intensities.

44. Apparatus for administering one or more product signals to one or more substances comprising:
   a) generating means for generating one or more product signals, each product signal being a function of a product capsule;
   b) applying means for applying said product signals to said substances.

45. Apparatus as recited in claim 44 wherein said generating means comprises means for generating one or more product signals, each product signal being a function of a product capsule and a dilution capsule.

46. Apparatus as recited in claim 45 further comprising means for receiving and storing one or more product capsules and one or more dilution capsules.

47. Apparatus as recited in claim 44 wherein said apparatus comprises a CIU.

48. Method for administering, to a desired area of application on a human body of a treatment subject, one or more therapeutic electromagnetic signals of electromagnetic waves or electric currents, each said signal stimulating a response in said human body which equals or approximates a response stimulated by a product corresponding to said signal, said method comprising the steps of:
   a) generating said electromagnetic signals, each said signal being a function of a sequence of binary numbers representing a corresponding product;
   b) applying said electromagnetic signals to said area of application.

49. Method as recited in claim 48 further comprising a step of producing and storing said sequences of binary numbers.

50. Method as recited in claim 49 wherein said step of producing said sequences of binary numbers comprises:
   a) generating and storing trial sequences of binary numbers and receiving, storing and comparing electrical resistance measurements;
   b) testing the electrical resistance of one or more test points on a human body of one or more test subjects before and after application of electromagnetic signals generated as a function said trial sequences of binary numbers;
   c) receiving said resistance measurements and transmitting and storing said resistance measurements.

51. Method as recited in claim 49 further comprising a step of producing and storing a plurality of dilution factors and wherein said functions utilize said dilution factors with said sequences of binary numbers to vary the amplitude of said electromagnetic signals.

52. Method as recited in claim 48 wherein said step of generating electromagnetic signals further comprises selecting one or more desired wave forms for said electromagnetic signals and generating said electromagnetic signals as a function of said sequences of binary numbers.

53. Method as recited in claim 48 wherein said step of generating electromagnetic signals further comprises selecting one or more desired wave forms for said electromagnetic signals and generating said electromagnetic signals as a function of said sequences of binary numbers and as a function of one or more dilution factors.

54. Method as recited in claim 48 further comprising providing a personal capsule unit for storing one or more said sequences of binary numbers and one or more dilution factors, generating one or more product signals as a function of said binary numbers and said dilution factors, and applying said product signals to said area of application.

55. Method as recited in claim 48 further comprising providing a personal tens unit for storing one or more said sequences of binary numbers and one or more dilution factors, generating one or more electric current product signals as a function of said binary numbers and said dilution factors, and applying said product signals to said area of application.

56. Method as recited in claim 48 wherein said step of applying said electromagnetic signals comprises transmitting said signals with a radio frequency transmitter and antenna.

57. Method as recited in claim 48 wherein said step of applying said electromagnetic signals comprises transmitting said signals with an infrared transmitter.

58. Method as recited in claim 48 wherein said step of applying said electromagnetic signals comprises transmitting said signals with a visible light transmitter and a fiber optic cable.

59. Method as recited in claim 48 wherein said step of applying said electromagnetic signals comprises transmitting said signals as electric currents through one or more conductors and applying said signals to said body of said treatment subject through one or more electrical contact pads.

60. Method as recited in claim 48 further comprising a step of imprinting a substance with one or more said signals through use of a capsule imprinter unit.

61. Method as recited in claim 48 further comprising a step of generating product signals with adjusted frequency and amplitude through use of a capsule generator unit.

62. Method as recited in claim 48 further comprising the step of administering a sound signal through use of an affirm unit.

63. Method as recited in claim 48 further comprising measuring the electrical resistance of said area of application.

64. Method for administering one or more product signals to a desired area of application on a human body of a treatment subject comprising the steps of:

a) generating one or more product signals, each product signal being a function of a product capsule;

b) applying said product signals to said area of application.

65. Method as recited in claim 64 further comprising a step of producing and storing product capsules for one or more products.

66. Method as recited in claim 65 wherein said step of producing product capsules comprises:

a) generating and storing trial product capsules and receiving, storing and comparing electrical resistance measurements;

b) testing the electrical resistance of one or more test points on a human body of one or more test subjects before and after application of product signals generated as a function said trial product capsules;

c) receiving and storing said resistance measurements.

67. Method as recited in claim 65 wherein said step of producing product capsules comprises producing and storing a plurality of dilution capsules and wherein said functions utilize said dilution capsules with said product capsules to vary the amplitude of said product signals.

68. Method as recited in claim 64 wherein said step of generating product signals further comprises selecting one or more desired wave forms for said product signals and generating said product signals as a function of said product capsules.

69. Method as recited in claim 64 wherein said step of generating product signals further comprises selecting one or more desired wave forms for said product signals and generating said product signals as a function of said product capsules and as a function of one or more dilution capsules.

70. Method as recited in claim 64 wherein said step of generating product signals comprises generating said product signals as a function of a product capsule and a dilution capsule.

71. Method as recited in claim 64 further comprising providing a personal capsule unit for storing one or more product capsules and one or more dilution capsules, generating one or more product signals as a function of said product capsules and said dilution capsules, and applying said product signals to said area of application.

72. Method as recited in claim 64 further comprising providing a personal tens unit for storing one or more product capsules and one or more dilution capsules, generating one or more electric current product signals as a function of said product capsules and said dilution capsules, and applying said product signals to said area of application.

73. Method as recited in claim 64 wherein said step of applying said product signals comprises transmitting said signals with a radio frequency transmitter and antenna.

74. Method as recited in claim 64 wherein said step of applying said product signals comprises transmitting said signals with an infrared transmitter.

75. Method as recited in claim 64 wherein said step of applying said product signals comprises transmitting said signals with a visible light transmitter and a fiber optic cable.

76. Method as recited in claim 64 wherein said step of applying said product signals comprises generating electric current product signals with an electric current generator, transmitting said electric current product signals through one or more conductors and applying said electric current product signals through one or more electrical contact pads.

77. Method as recited in claim 64 further comprising a step of imprinting one or more substances with a capsule imprinter unit.

78. Apparatus as recited in claim 64 further comprising a step of generating product signals with adjusted frequency and amplitude through use of a capsule generator unit.

79. Apparatus as recited in claim 64 further comprising a step of generating a sound signal through use of an affirm unit.

80. Method as recited in claim 64 further comprising a step of measuring the electrical resistance of said area of application.

81. Method as recited in claim 64 further comprising a step of receiving and storing one or more product capsules and one or more dilution capsules.

82. Method as recited in claim 64 further comprising the step of measuring the electrical resistance of area of application of one or more product signals before and after application of said product signals.

83. Method as recited in claim 64 further comprising storing one or more product capsules and one or more dilution capsules in a portable device and using said portable device to generate and apply one or more product signals to desired areas of application.

84. Method as recited in claim 64 further comprising a step of simultaneously generating two or more product signals with the frequency and intensity of each of said product signals being separately adjusted as desired by the user.

85. Method as recited in claim 64 further comprising a step of applying one or more product signals to imprint one or more substances with said product signal.

86. Method as recited in claim 64 further comprising a step of storing one or more product capsules and one or more dilution capsules in memory, generating one or more product signals as a function of said product capsules and dilution capsules, and transmitting said product signals in one or more selected wave forms, one or more selected frequencies, and one or more selected intensities.

87. Method for administering one or more product signals to one or more substances comprising steps of:
 a) generating one or more product signals, each product signal being a function of a product capsule;
 b) applying said product signals to said substances.

88. Method as recited in claim 87 wherein said step of generating product signals comprises generating one or more product signals, each product signal being a function of a product capsule and a dilution capsule.

89. Method as recited in claim 87 further comprising a step of receiving and storing one or more product capsules and one or more dilution capsules.

90. Method for generating product capsules for a product comprising:
 a) measuring the electrical resistance of one or more test points on a human body of one or more test subjects;
 b) subjecting said subjects to said product;
 c) measuring any change in electrical resistance at each of said test points for each of said subjects in response to being subjected to said product;
 d) removing said product from said subjects;
 e) subjecting said subjects to product signals generated from one or more trial product capsules and measuring the electrical resistance response at each said test point for each said subject until a product capsule is found from which a product signal is generated which causes an electrical resistance response in said subjects which equals or approximates the response produced by said product.

* * * * *

US006142927C1

(12) EX PARTE REEXAMINATION CERTIFICATE (5824th)
United States Patent
Clark

(10) Number: US 6,142,927 C1
(45) Certificate Issued: Jul. 24, 2007

(54) METHOD AND APPARATUS FOR TREATMENT WITH RESONANT SIGNALS

(76) Inventor: James Hoyt Clark, 432 N. 750 East, Lindon, UT (US) 84042

Reexamination Request:
No. 90/006,126, Oct. 9, 2001
No. 90/007,076, Jun. 14, 2004

Reexamination Certificate for:
Patent No.: 6,142,927
Issued: Nov. 7, 2000
Appl. No.: 09/152,195
Filed: Sep. 14, 1998

(51) Int. Cl.
*A61B 17/52* (2006.01)
*A61N 2/00* (2006.01)
*A61N 19/00* (2006.01)

(52) U.S. Cl. .......................................... 600/9; 128/897
(58) Field of Classification Search ...................... None
See application file for complete search history.

(56) References Cited

U.S. PATENT DOCUMENTS 4,858,609 A * 8/1989 Cole ........................... 607/91
5,629,286 A 5/1997 Brewitt
6,142,927 A 11/2000 Clark

OTHER PUBLICATIONS

Curtin, Howard R. Ph.d., Part 1—Introduction to Applied P3 Technology A Framework for EAV, Muscle Testing, Dowsing, and Other Interrogatory Biofeedback Procedures, Townsend Letter for Doctors & Patients, (Jan. 1997, #162).

Office Action in Ex Parte Reexamination, Appl. Control. No. 90/006,126; Patent No. 614297.

Becker RO; *Cross Currents*, pp. 67–247, 1990.

Benveniste J; *Transfer of Biological Activity by Electromagnetic Fields*; Frontier perspectives, vol. 3, pp. 13–15; fall, 1993.

Chen KG; *III. Applying Quantum Interference to EDST Medicine Testing*; IEEE Engineering in Medicine & Biology, pp. 64–66; May/Jun., 1996.

Clark JH; *The Politics and Science of Electrodermal Screening*; 1997.

Clark JH; *Listen System Investigational Plan*; 1997.

Clark JH; *The Life Information System Ten, Online User Manual*; 1996.

Clark JH, et al; *Computerized ElectroDermal Screening (CEDS) Introductory Course*; 1990.

Clark JH and Clark WH; *The Listen System Step–by–Step Manual*, 1994.

Clark JH; *Advance Training Course Biosource Inc.*

Clark JH; *Listen Online Manual*; 1997.

Krop J, Swierczek, Wood A; *Comparison of Ecological Testing with the Vega Test Method in Identifying Sensitivities to Chemicals, Foods and Inhalants*; Am J Acupunct., vol. 13, pp. 253–259; Jul.–Sep. 1985.

Lam FMK, Tsuei J; *Case Findings from a Family Practitioner's Office Using Electroacupuncture According to Voll*; Am J Acupunct., vol. 11, pp. 23–28; Jan.–Mar., 1983.

(Continued)

*Primary Examiner*—Beverly M. Flanagan

(57) ABSTRACT

This invention is a method and apparatus for applying low energy, non-ionizing, nonthermal, electromagnetic radiation or electric current to the body of a subject for therapeutic and health promoting purposes. Digital sequences, referred to as product capsules, representing natural or manufactured substances are stored in a computer. The computer is interfaced with the apparatus of the present invention which generates electromagnetic signals or electric currents, referred to as product signals, corresponding to the product capsules, which have been found to stimulate a response in the human body of a subject which is equal or approximately equal to the response stimulated by the corresponding substances. The product signals resonate with the body of the subject at the cellular level. The apparatus provides for the application of the resonant product signals to the subject through an antenna, an infrared transmitter, audio speakers or direct contact to the skin.

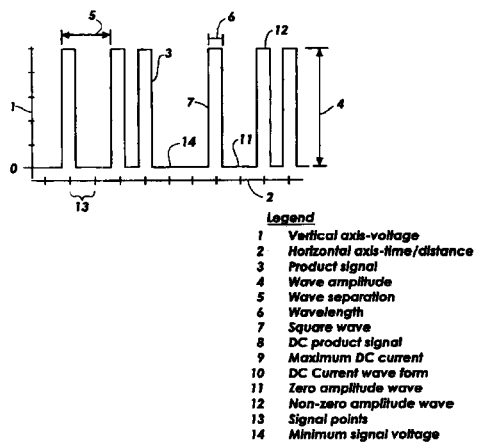

OTHER PUBLICATIONS

Lawler JC, Davis MJ, Griffith EC; *Electrical Characteristics of the Skin*; J Investigative Dermatology, vol. 3, pp. 301–308; 1960.

Reichamanis M, Marino AA, Becker RO; *Electrical Correlates of Acupuncture Points*; IEEE Trans.Biomedical Engin., pp. 533–535; Nov. 1975.

Reichamanis M. Marion AA, Becker RO; *Laplace Plane Analysis of Impedance Between Acupuncture Points H–3 and H–4*; Comp. Medicine East & West, vol. .V, pp. 289–295; 1977.

Royal FF, et al; *Physician's Electro–Diagnostic Handbook*; 1993.

Rosendal T; *Studies on the Conducting Properties of the Human Skin to Direct Current*; Acta Physiol. Scand., vol. 5, pp. 130–151; 1943.

Rubik B, Becker RO, Flower RG, Hazelwood CF, Liboff AR, Walleczek J; *Bioeelctromagenetics Applications in Medicine*; Alternative Medicine: Expanding Medical Horizons, pp. 45–65; 1994.

Saita H; *Modern Scientific Medical Acupuncture*; J Am Osteopath Assoc, vol. 72, pp. 685/47–696/58; 1973.

Tenforde TS and Kaune, WT; *Interaction of Extremely Low Frequency Electric and Magnetic Fields with Humans*; Health Physics, vol. 53, pp. 585–606; 1987.

Tiller WA; *On the Explanation of Electrodermal Diagnostic and Treatment Instruments, Part 1: The Electrical Behavior of Human Skin*; 1985.

Tiller WA; *Some Physical Network Characteristics of Acupuncture Points and Meridians*; pp. 37–69; Jun. 1972.

Voll R; *The 850 EAV Measurement Points of the Meridians and Vessels Including the Secondary Vessels*; 1983.

Voll R; *Interrelations of Odontons and Tonsils to Organs, Fields of Disturbance, and Tissue Systems*; 1978.

Voll R; *The Phenomenon of Medicine Testing in Electroacupuncture According to Voll*; Am J Acupunct, vol. 8, pp. 97–104; Apr.–Jun., 1980.

Voll R; *Topographic Positions of the Measurement Points in Electro–Acupuncture*; 1977.

Walleczek J; *Electromagnetic Field Effects on Cells of the Immune System: the Role of Calcium Signaling*; FASEB J, vol.. 6, pp. 3177–3185; Oct. 1992.

Zong–xiang Z; *Research Advances in the Electrical Specificity of meridians and Acupuncture Points*; Am J of Acupunct, vol. 9, pp. 203–216; Jul.–Sep., 1981.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9, 12, 26, 29, 44-47, 56, 59, 73, 76 and 87-90 are cancelled.

Claims 1, 10, 11, 17, 27, 28 and 48, 57, 58, 64, 74, 75 are determined to be patentable as amended.

Claims 2-8, 13-16, 18-25 and 30-43, 49-55, 60-63, 65-72, 77-86 dependent on an amended claim, are determined to be patentable.

1. Apparatus for administering, to a desired area of application on a human body of a treatment subject, one or more therapeutic electromagnetic signals of electromagnetic waves or electric currents, each said signal stimulating a response in said human body which equals or approximates a response simulated by a product corresponding to said signal, said apparatus comprising:
   a) generating means for generating said electromagnetic signals, each said signal being a function of a sequence of binary numbers representing a corresponding product;
   b) [applying means] *radio frequency transmitter and antenna* for applying said electromagnetic signals to said area of application.

10. [Apparatus as recited in claim 1 wherein said applying means comprises an] *Apparatus for administering to a desired area of application on a human body of a treatment subject, one or more therapeutic electromagnetic signals of electromagnetic waves or electric currents, each said signal stimulating a response in said human body which equals or approximates a response stimulated by a product corresponding to said signal, said apparatus comprising:*
   *a) generating means for generating said electromagnetic signals, each said signal being a function of a sequence of binary numbers representing a corresponding product;*
   b) infrared transmitter *for applying said electromagnetic signals to said area of application.*

11. [Apparatus as recited in claim 1 wherein said applying means comprises a] *Apparatus for administering to a desired area of application on a human body of a treatment subject, one or more therapeutic electromagnetic signals of electromagnetic waves or electric currents, each said signal stimulating a response in said human body which equals or approximates a response stimulated by a product corresponding to said signal, said apparatus comprising:*
   *a) generating means for generating said electromagnetic signals, each said signal being a function of a sequence of binary numbers representing a corresponding product;*
   b) visible light transmitter and a finer optic cable *for applying said electromagnetic signals to said area of application.*

17. Apparatus for administering one or more product signals to a desired area of application on a human body of a treatment subject comprising:
   a) generating means for generating one or more product signals, each product signal being a function of a product capsule;
   b) [applying means] *radio frequency transmitter and antenna* for applying said product signals to said area of application.

27. [Apparatus as recited in claim 17 wherein said applying means comprises an] *Apparatus for administering one or more product signals to a desired area of application on a human body of a treatment subject comprising:*
   *a) generating means for generating one or more product signals, each product signal being a function of a product capsule;*
   b) infrared transmitter *for applying said electromagnetic signals to said area of application.*

28. [Apparatus as recited in claim 17 wherein said applying means comprises a] *Apparatus for administering one or more product signals to a desired area of application on a human body of a treatment subject comprising:*
   *a) generating means for generating one or more product signals, each product signal being a function of a product capsule;*
   b) visible light transmitter and a fiber optic cable *for applying said electromagnetic signals to said area of application.*

48. Method for administering, to a desired area of application on a human body of a treatment subject, one or more therapeutic electromagnetic signals of electromagnetic waves or electric currents, each said signal stimulating a response in said human body which equals or approximates a response stimulated by a product corresponding to said signal, said method comprising the steps of:
   a) generating said electromagnetic signals, each said signal being a function of a sequence of binary numbers representing a corresponding product;
   b) applying said electromagnetic signals *by transmitting said signals with a radio frequency transmitter and antenna* to said area of application.

57. [Method as recited in claim 48 wherein said step of applying said electromagnetic signals comprises] *Method for administering to a desired area of application on a human body of treatment subject, one or more therapeutic electromagnetic signals of electromagnetic waves or electric currents, each said signal stimulating a response in said human body which equals or approximates a response stimulated by a product corresponding to said signal, said method comprising the steps of:*
   *a) generating said electromagnetic signals, each said signal being a function of a sequence of binary numbers representing a corresponding product;*
   b) applying said electromagnetic signals by transmitting said signals with an infrared transmitter *to said area of application.*

58. [Method as recited in claim 48 wherein said step of applying said electromagnetic signals comprises] *Method for administering to a desired area of application on a human body of a treatment subject, one or more therapeutic electromagnetic signals of electromagnetic waves or electric currents, each said signal stimulating a response in said human body which equals or approximates a response stimulated by a product corresponding to said signal, said method comprising the steps of:*

*a) generating said electromagnetic signals, each said signal being a function of a sequence of binary numbers representing a corresonding product;*

*b) applying said electromagnetic signals by transmitting said signals with a visible light transmitter and a fiber optic cable to said area of application.*

64. Method for administering one or more product signals to a desired area of application on a human body of a treatment subject comprising the steps of:

a) generating one or more product signals, each product signal being a function of a product capsule;

b) applying said product signals *by transmitting said signals with a radio frequency transmitter and antenna* to said area of application.

74. [Method as recited in claim 64 wherein said step of applying said product signals comprises] *Method for administering one or more product signals to a desired area of application on a human body of a treatment subject comprising the steps of:*

*a) generating one or more product signals, each product signal being a function of a product capsule;*

*b) applying said product signals by transmitting said signals with an infrared transmitter to said area of application.*

75. [Method as recited in claim 64 wherein said step of applying said product signals comprises] *Method for administering one or more product signals to a desired area of application on a human body of a treatment subject comprising the steps of:*

*a) generating one or more product signals, each product signal being a function of a product capsule;*

*b) applying said product signals by transmitting said signals with a visible light transmitter and a fiber optic cable to said area of application.*

* * * * *

(12) EX PARTE REEXAMINATION CERTIFICATE (8915th)
United States Patent
Clark

(10) Number: US 6,142,927 C2
(45) Certificate Issued: Mar. 20, 2012

(54) METHOD AND APPARATUS FOR TREATMENT WITH RESONANT SIGNALS

(76) Inventor: James Hoyt Clark, Lindon, UT (US)

Reexamination Request:
No. 90/008,777, Nov. 5, 2007

Reexamination Certificate for:
Patent No.: 6,142,927
Issued: Jul. 24, 2007
Appl. No.: 09/152,195
Filed: Sep. 14, 1998

Reexamination Certificate B1 6,142,927 issued Nov. 7, 2000

(51) Int. Cl.
*A61N 2/00* (2006.01)
*A61N 1/40* (2006.01)
*A61N 1/32* (2006.01)

(52) U.S. Cl. ............................................ 600/9; 128/897
(58) Field of Classification Search ................... None
See application file for complete search history.

(56) References Cited

To view the complete listing of prior art documents cited during the proceeding for Reexamination Control Number 90/008,777, please refer to the USPTO's public Patent Application Information Retrieval (PAIR) system under the Display References tab.

*Primary Examiner* — Jeanne M. Clark

(57) ABSTRACT

This invention is a method and apparatus for applying low energy, non-ionizing, nonthermal, electromagnetic radiation or electric current to the body of a subject for therapeutic and health promoting purposes. Digital sequences, referred to as product capsules, representing natural or manufactured substances are stored in a computer. The computer is interfaced with the apparatus of the present invention which generates electromagnetic signals or electric currents, referred to as product signals, corresponding to the product capsules, which have been found to stimulate a response in the human body of a subject which is equal or approximately equal to the response stimulated by the corresponding substances. The product signals resonate with the body of the subject at the cellular level. The apparatus provides for the application of the resonant product signals to the subject through an antenna, an infrared transmitter, audio speakers or direct contact to the skin.

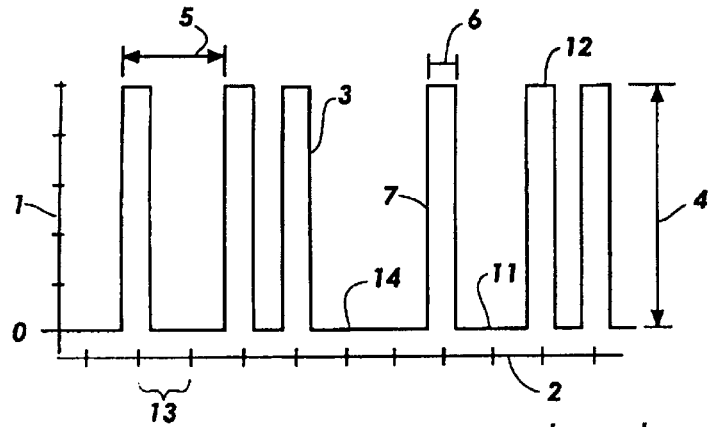

Legend
1  Vertical axis-voltage
2  Horizontal axis-time/distance
3  Product signal
4  Wave amplitude
5  Wave separation
6  Wavelength
7  Square wave
8  DC product signal
9  Maximum DC current
10 DC Current wave form
11 Zero amplitude wave
12 Non-zero amplitude wave
13 Signal points
14 Minimum signal voltage

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9, 12, 26, 29, 44-47, 56, 59, 73, 76 and 87-90 were previously cancelled.

Claims 1-8, 13-25, 30-43, 48-55, 60-72 and 77-86 are cancelled.

Claims 10, 11, 27, 28, 57, 58, 74 and 75 were not reexamined.

\* \* \* \* \*